United States Patent [19]

Chatterjee

[11] Patent Number: 5,744,339
[45] Date of Patent: Apr. 28, 1998

[54] THIOMETHYLENE GROUP-CONTAINING ALDEHYDE CYSTEINE AND SERINE PROTEASE INHIBITORS

[75] Inventor: Sankar Chatterjee, Wynnewood, Pa.

[73] Assignee: Cephalon, Inc., West Chester, Pa.

[21] Appl. No.: 706,184

[22] Filed: Aug. 30, 1996

[51] Int. Cl.[6] .............................. C12N 9/99; C12N 9/48; C07C 321/00; A01N 37/18
[52] U.S. Cl. ......................... 435/184; 435/219; 564/162; 514/618
[58] Field of Search .................................. 435/219, 184, 435/212; 564/162; 514/618

[56] References Cited

U.S. PATENT DOCUMENTS

| | | | |
|---|---|---|---|
| 4,219,497 | 8/1980 | Plattner et al. | 548/542 |
| 4,499,082 | 2/1985 | Shenvi et al. | 514/2 |
| 4,537,773 | 8/1985 | Shenvi | 514/63 |

FOREIGN PATENT DOCUMENTS

WO 92/14696  9/1992  WIPO.

OTHER PUBLICATIONS

Puri et al. "Modulation of thrombin–induced platelet aggregation by inhibition of calpain by a synthetic peptide derived from the thiol–protease inhibitory sequence of kininogens and S–(3–nitro–2–pyridinesulfenyl)–cysteine", Eur. J. Biochem. (1993) vol. 2, pp. 233–241.

Davis et al., "Chemistry of Oxaziridines. 9. Synthesis of 2–Sulfonyl–and 2–Sulfamyloxaziridines Using Potassium Peroxymonosulfate (Oxone)", *J. Org. Chem.*, 1988, 53, 2087–2089.

Greene, T.W. and Wuts, P.G.M., *Protective Groups in Organic Synthesis*, 2d. Ed., Wiley & Sons, 1991. Publ. in NY.

Lee, W.J. et al., "Factors Influencing the Bindingof Calpain I to Human Erythrocyte Inside–Out Vesicles", *Biochem Int'l.*, 1990, 22(1), 163–171.

Lehninger, *Biochemistry*, Second Edition, Worth Publishers, Inc., 1975, 73–75, Published in NY.

Luly, J. R. et al., "A Synthesis of Protected, Aminoalkyl Epoxides from α–Amino Acids", *J. Org. Chem.*, 1987, 52, 1487–1492.

*Remington's Pharmaceutical Sciences*, Mack Publishing Company, Easton, PA, 1980.

Chatterjee, et al., "Potent Fluoromethyl Ketone Inhibitors of Recombinant Human Calpain I[+]", *Bioorganic & Medicinal Chem.Letters*, 1996, 6, 1237–1240.

*Primary Examiner*—Jean C. Witz
*Assistant Examiner*—Susan Hanley
*Attorney, Agent, or Firm*—Woodcock Washburn Kurtz Mackiewicz & Norris LLP

[57] ABSTRACT

The present invention is directed to thiomethylene group-containing aldehyde inhibitors of cysteine or serine proteases. Methods for the use of the protease inhibitors are also described.

16 Claims, No Drawings

THIOMETHYLENE GROUP-CONTAINING ALDEHYDE CYSTEINE AND SERINE PROTEASE INHIBITORS

FIELD OF THE INVENTION

Novel thiomethylene group-containing aldehyde inhibitors of cysteine or serine proteases, methods for making these novel compounds, and methods for using the same are disclosed.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypoanosoma cruzi*, malaria parasites *Plasmodium falciparum* and *P.vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation ascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to novel cysteine and serine protease inhibitors which contain a thiomethylene group adjacent to the P2 position (where the P2 position is the position adjacent to the site of catalysis). They are represented by the following Formula I:

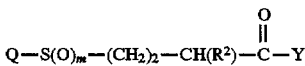

wherein:

Q is aryl having from about 6 to about 14 carbons, heteroaryl having from about 6 to about 14 ring atoms, aralkyl having from about 7 to about 15 carbons, heteroalkyl having from 2 to about 7 carbons, or arylheteroalkyl wherein the aryl portion can be unfused or fused with the heteroalkyl ring;

m is 0, 1, or 2;

Y has the formula:

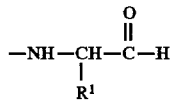

wherein:

$R^1$ and $R^2$ are independently H, alkyl having from one to about 14 carbons, cycloalkyl having from 3 to about 10 carbons, or a natural or unnatural side chain of an L-amino acid, said alkyl and cycloalkyl groups being optionally substituted with one or more J groups; and J is halogen, lower alkyl, aryl, heteroaryl, amino optionally substituted with one to three aryl or lower alkyl groups, guanidino, alkoxycarbonyl, alkoxy, hydroxy, or carboxy.

In some preferred embodiments of the compounds of Formula I, m is 1 or 2. In further preferred embodiments of the compounds of Formula I, $R^2$ is isobutyl, $R^1$ is isobutyl, benzyl, or ethyl, m is 2, and Q is 2-naphthyl.

The compounds of the invention are useful for the inhibition of cysteine and serine proteases. Beneficially, the compounds find utility in a variety of settings. For example, in a research arena, the claimed compounds can be used, for example, as standards to screen for natural and synthetic cysteine protease and serine protease inhibitors which have the same or similar functional characteristics as the disclosed compounds. In a clinical arena,, the compounds can be used to alleviate, mediate, reduce and/or prevent disorders which are associated with abnormal and/or aberrant activity of cysteine proteases and/or serine proteases. Accordingly, methods for using the subject compounds, such as methods for inhibiting serine proteases or cysteine proteases comprising contacting said proteases with an inhibitory amount of a compound of the invention are disclosed. Methodologies for making the present thiomethylene group-containing inhibitors are also disclosed. These and other features of the compounds of the subject invention are set forth in more detail below.

DETAILED DESCRIPTION

Novel cysteine and serine protease inhibitors have been discovered which are represented by the general Formula I:

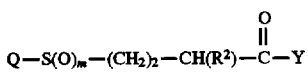

wherein:

Q is aryl having from about 6 to about 14 carbons, heteroaryl having from about 6 to about 14 ring atoms, aralkyl having from about 7 to about 15 carbons, heteroalkyl having from 2 to about 7 carbons, or arylheteroalkyl wherein the aryl portion can be unfused or fused with the heteroalkyl ring;

m is 0, 1, or 2;

Y has the formula:

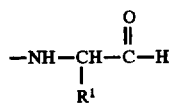

$R^1$ and $R^2$ are independently H, alkyl having from one to about 14 carbons, cycloalkyl having from 3 to about 10 carbons, or a natural or unnatural side chain of an L-amino acid, said alkyl and cycloalkyl groups being optionally substituted with one or more J groups; and J is halogen, lower alkyl, aryl, heteroaryl, amino optionally substituted with one to three aryl or lower alkyl groups, guanidino, alkoxycarbonyl, alkoxy, hydroxy, or carboxy.

In some preferred embodiments of the compounds of Formula I, $R^2$ is isobutyl. In other preferred embodiments of the compounds of Formula I, $R^1$ is isobutyl, benzyl, or ethyl. In further preferred embodiments of the compounds of Formula I, Q is 2-naphthyl.

In especially preferred embodiments $R^2$ is isobutyl, $R^1$ is isobutyl, and Q is 2-naphthyl.

As used herein, the term "alkyl" is meant to include straight-chain, branched and cyclic hydrocarbon groups such as, for example, ethyl, isopropyl and cyclopropyl groups. Preferred alkyl groups have 1 to about 10 carbon atoms. "Cycloalkyl" groups are cyclic alkyl groups. "Aryl" groups are aromatic cyclic compounds including but not limited to phenyl, tolyl, naphthyl, anthracyl, phenanthryl, pyrenyl, and xylyl. Preferred aryl groups include phenyl and naphthyl. The term "carbocyclic", as used herein, refers to cyclic groups in which the ring portion is composed solely of carbon atoms. The term "heterocyclic" refers to cyclic groups in which the ring portion includes at least one heteroatom such as O, N or S. "Heteroalkyl" groups are heterocycles containing solely single bonds within their ring portions, i.e. saturated heteroatomic ring systems. The term "lower alkyl" refers to alkyl groups of 1–4 carbon atoms. The term "halogen" refers to F, Cl, Br, and I atoms.

The term "aralkyl" denotes alkyl groups which bear aryl groups, for example, benzyl groups. The term "heteroaryl" denotes aryl groups having one or more heteroatoms contained within an aromatic ring. "Heteroaralkyl" groups are aralkyl groups which have one or more heteroatoms in their aromatic ring portion.

As used herein, the term "amino acid" denotes a molecule containing both an amino group and a carboxyl group. As used herein the term "L-amino acid" denotes an α-amino acid having the L configuration around the α-carbon, that is, a carboxylic acid of general formula CH(COOH)(NH$_2$)-(sidechain), having the L-configuration. Sidechains of L-amino acids include naturally occurring and non-naturally occurring moieties. Nonnaturally occurring amino acid sidechains are moieties that are used in place of naturally occurring amino acid sidechains in, for example, amino acid analogs. See, for example, Lehninger, *Biochemistry*, Second Edition, Worth Publishers, Inc, 1975, pages 73–75. Representative α-amino acid sidechains are shown below on Table 1.

TABLE 1

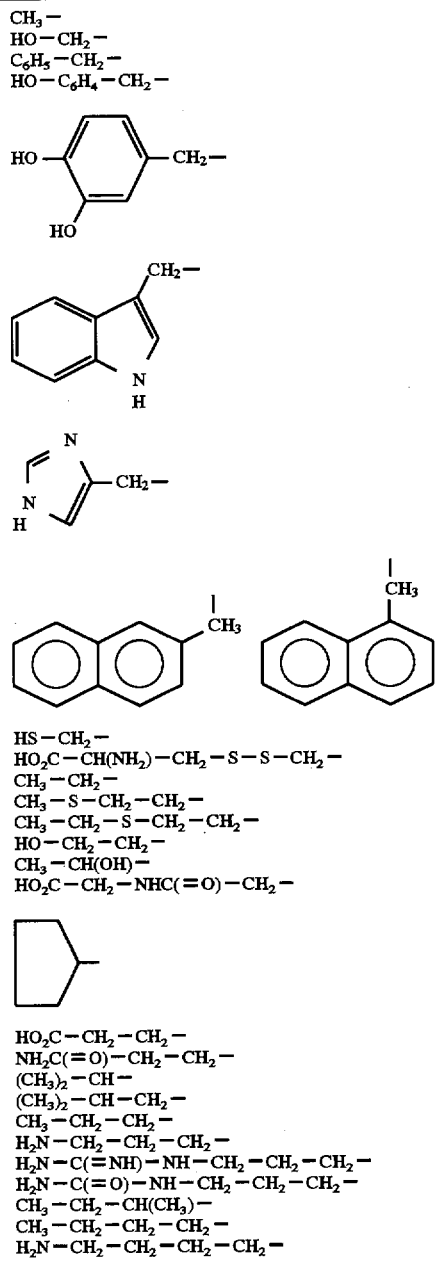

Functional groups present on the compounds of Formula I may contain protecting groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other protecting groups include the phthalimido group, arylcarbonyls, alkylcarbonyls, alkoxycarbonyls, aryloxycarbonyls, aralkyloxycarbonyls, alkyl- and aralkylsulfonyls, and arylsulfonyl groups such as those which have the following formulas:

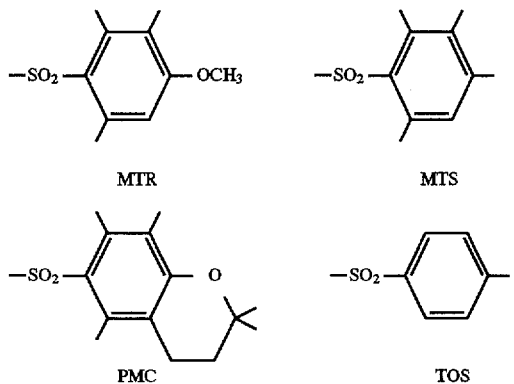

Other preferred protecting groups according to the invention may be found in Greene, T. W. and Wuts, P. G. M., "Protective Groups in Organic Synthesis" 2d. Ed., Wiley & Sons, 1991.

Because the thiomethylene group-containing components of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration. Typically, the formulations are administered at lower dosage levels and increased until the desired inhibitory effect is achieved.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Compounds of the invention were prepared by the following procedures. $R_f$ values are reported using standard silica gel and analytical plates.

The synthesis of compounds of general Formula 1–10 are summarized in Scheme I below:

which time the temperature had increased to room temperature. The reaction mixture was then poured into an ice-water mixture (100 mL) and extracted into ether (3×100 mL). The combined organic layer was washed with water (2×25 mL), brine (1×20 mL), dried (MgSO$_4$), and concentrated to give a crude product which was purified by flash silica gel column chromatography (eluant: 3% ethyl acetate in hexanes) to give 12.20 g of compound 2.

Compound 2: Colorless oil; $R_f$ (5% ethyl acetate in hexanes): 0.25; $^1$H-NMR (300 MHz, CDCl$_3$) δ 7.80 (t, 4H), 7.50 (m, 3H), 4.15 (q, 2H), 3.10 (t, 2H), 2.50 (t, 2H), 2.00 (2 overlapping t, 2H), 1.25 (t, 3H).

Example 2

Synthesis of Intermediate 3

To a cooled (−78° C.) solution of lithium diisopropylamide (0.053 mol, prepared in situ from the nBuLi and diisopropylamine) in THF (40 mL)—heaxane (21 mL) was added slowly a solution of compound 2 (12.13 g, 0.044 mol) in anhydrous THF (20 mL). The mixture was stirred for 1 hour and to it was added a solution of 1-iodo-2-methylpropane (9.76 g, 0.053 mol) in hexamethyl phosphoramide (9.23 mL). The mixture was stirred for another 3 hours, by which time the temperature had slowly increased to room temperature. The reaction mixture was quenched

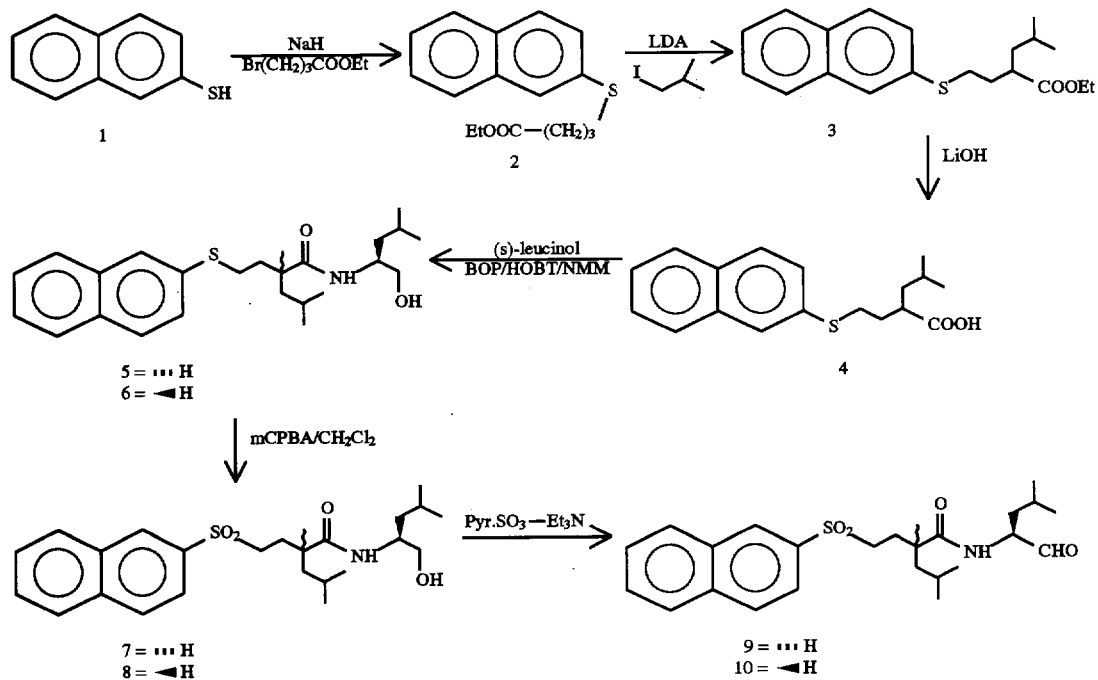

Scheme I

Example 1

Synthesis of Intermediate 2

To a stirred mixture of NaH (60% in oil, 2.04 g, 0.05 mol) in anhydrous THF (20 mL) at 0° C. was added slowly a solution of 2-naphthalenethiol (1, 7.79 g, 0.048 mol) in anhydrous THF (20 mL). The mixture was stirred for 30 minutes. A solution of ethyl 4-bromobutyrate (10.43 g, 0.053 mol) in anhydrous THF (20 mL) was slowly added to the reaction flask. The mixture was stirred for another hour, by with saturated NH$_4$Cl (50 mL), diluted with water (50 mL), and extracted into ether (3×100 mL). The combined organic layer was washed with brine (1×30 mL), dried (MgSO$_4$), and concentrated to give a crude product which was purified by flash silica gel column chromatography (eluant: 2% ethyl acetate in hexanes) to give 4.60 g of compound 3.

Compound 3: Colorless oil; $R_f$ (5% ethyl acetate in hexanes): 0.37; $^1$H-NMR (300 MHz, CDCl$_3$) δ 7.80 (t, 4H), 7.50 (m, 3H), 4.15 (q, 2H), 3.00 (m, 2H), 2.65 (m, 1H), 2.00 (m, 1H), 1.80 (m, 1H), 1.60 (m, 3H), 1.25 (t, 3H), 0.90 (t, 6H).

Example 3

Synthesis of Intermediate 4

A mixture of compound 3 (4.53 g, 0.014 mol), lithium hydroxide monohydrate (2.30 g, 0.055 mol), ethanol (60 mL) and water (15 mL) was gently refluxed for 3 hours. Ethanol was removed in vacuo and the basic aqueous layer was washed with ether (2×20 mL), acidified with dilute acid, and extracted into ethyl acetate (3×50 mL). The combined organic layer was washed with brine (1×20 mL), dried (MgSO$_4$), and concentrated to give 3.80 g of compound 4 which was used without further purification.

Compound 4: White solid, mp 76°–78° C.; $^1$H-NMR (300 MHz, CDCl$_3$) δ 7.80 (t, 4H), 7.40 (m, 3H), 3.00 (m, 2H), 2.70 (m, 1H), 2.00 (m, 1H), 1.80 (m, 1H), 1.60 (m, 2H), 1.25 (m, 1H), 0.90 (t, 6H)

Example 4

Synthesis of Intermediates 5 and 6

To a cooled (0° C.) solution of compound 4 (3.35 g, 0.011 mol) in anhydrous DMF (20 mL) was added N-methylmorpholine (3.36 g, 0.033 mol) followed by 1-HOBt (1.50 g, 0.011 mol) and BOP (4.90 g, 0.011 mol). The mixture was stirred for 15 minutes and to it was added (S)-leucinol (1.70 g, 0.0143 mol). The cooling bath was removed and the mixture was stirred for 4 hours, poured into ice-water (50 mL), and extracted into ethyl acetate (3×60 mL). The organic layer was washed with 2% citric acid solution (2×25 mL), saturated sodium bicarbonate solution (2×25 mL), brine (1×25 mL), and dried over anhydrous sodium sulfate. Solvent evaporation under reduced pressure gave a mixture of compounds 5 and 6. Separation by column chromatography (silica gel, 30% ethyl acetate in hexanes) produced 0.95 g of 5 and 1.10 g of 6, respectively.

Compound 5: White solid, mp 96°–98° C.; R$_f$ (50% ethyl acetate in hexanes): 0.51; $^1$H-NMR (300 MHz, CDCl$_3$) δ 7.80 (t, 4H), 7.45 (m, 3H), 5.65 (d, 1H), 4.05 (m, 1H), 3.60 (m, 1H),, 3.40 (m, 1H), 3.15 (m, 1H), 3.00 (m, 1H), 2.80 (b, 1H), 2.50 (m, 1H), 2.00 (m, 1H), 1.80–1.10 (m, 7H), 0.90 (m, 12H).

Compound 6: White solid, mp 85°–90° C.; R$_f$ (50% ethyl acetate in hexanes): 0.40; $^1$H-NMR (300 MHz, CDCl$_3$) δ 7.80 (m, 4H), 7.45 (m, 3H), 5.70 (d, 1H), 4.05 (m, 1H), 3.65 (m, 1H), 3.55 (m, 1H), 3.15 (m, 1H), 2.90 (m, 2H), 2.50 (m, 1H), 2.00 (m, 1H), 1.80–1.40 (m, 4H), 1.40–1.10 (m, 3H), 0.90 (t, 6H), 0.80 (t, 6H).

Example 5

Synthesis of Intermediates 7 and 8

To a solution of compound 5 (0.065 g, 0.1618 mmol) in methylene chloride (3 mL) at 0° C. was added m-chloroperbenzoic acid (95%, 0.062 g, 0.356 mmol) in methylene chloride (2 mL). The cooling bath was removed, the mixture was stirred for another 30 minutes, and then washed successively with 5% sodium thiosulfite solution (2×5 mL), water (1×5 mL), 3% NaHCO$_3$ solution (2×5 mL), and brine (1×5 mL). Drying (Na$_2$SO$_4$) and solvent evaporation generated 0.070 g of compound 7 which was used without further purification. In a similar way, 0.065 g of compound 6 was converted to 0.70 g of compound 8.

Compound 7: White solid, mp 112°–114° C.; R$_f$ (60% ethyl acetate in hexanes): 0.35; $^1$H-NMR (300 MHz, CDCl$_3$) δ 8.50 (s, 1H), 8.00 (m, 3H), 7.85 (d, 1H), 7.65 (m, 2H), 6.05 (d, 1H), 4.15 (m, 1H), 3.80 (dd, 1H), 3.50 (m 1H), 3.40 (m, 1H), 3.20 (m, 1H), 2.80 (m, 2H), 2.00 (m, 2H), 1.60–1.40 (m, 5H), 1.20 (m, 1H), 0.90 (m, 12H).

Compound 8: White solid, mp 112°–115° C.; R$_f$ (60% ethyl acetate in hexanes): 0.32; $^1$H-NMR (300 MHz, CDCl$_3$) δ 8.50 (s, 1H), 8.00 (m, 3H), 7.85 (d, 1H), 7.70 (m, 2H), 6.00 (d, 1H), 4.05 (m, 1H), 3.65 (m, 1H), 3.55 (m 1H), 3.20 (m, 2H), 2.65 (m, 2H), 2.00 (q, 2H), 1.60 (m, 3H), 1.40 (m, 2H), 1.20 (m, 1H), 0.90 (m, 12H).

Example 6

Synthesis of Aldehydes 9 and 10

To a cooled (0° C.) solution of compound 7 (0.063 g, 0.145 mmol) in anhydrous methylene chloride (3 mL) and anhydrous dimethyl sulfoxide (3 mL) was added triethylamine (0.073 g, 0.58 mmol). Sulfur trioxide-pyridine complex (0.060 g, 0.58 mmol) was slowly added to the stirred mixture over a period of 5 minutes and the ice bath was removed. The mixture was stirred for another hour, poured into water (5 mL) and extracted into ether (3×10 mL). The organic layer was washed with 2% citric acid solution (2×5 mL), saturated sodium bicarbonate solution (2×5 mL), brine (1×5 mL), and dried over anhydrous magnesium sulfate. Solvent evaporation gave a residue which was washed with n-pentane (19 mL) and dried under vacuum to produce 0.040 g of compound 9. A general description of this oxidation procedure can be found in Luly, J. R. et. al. *J. Org. Chem.* 1987, 52, 1488.

In a similar way, 0.063 g of compound 8 was converted to 0.034 g of the aldehyde, compound 10.

Compound 9: White solid, mp 104°–109° C. (softening to melt); R$_f$ (70% ethyl acetate in hexanes): 0.87; $^1$H-NMR (300 MHz, CDCl$_3$) δ 9.60 (s, 1H), 8.55 (s, 1H), 8.00 (m, 4H), 7.70 (m, 2H), 6.40 (d, 1H), 4.65 (m, 1H), 3.65 (m, 1H), 3.20 (m, 1H), 2.80 (m, 1H), 2.10 (m, 1H), 1.90 (m, 1H), 1.60–1.40 (m, 5H), 1.20 (m, 1H), 0.90 (m, 12H).

Compound 10: White gum, R$_f$ (70% ethyl acetate in hexanes): 0.83; $^1$H-NMR (300 MHz, CDCl$_3$) δ 9.60 (s, 1H), 8.45 (s, 1H), 8.00 (m, 3H), 7.85 (d, 1H), 7.70 (m, 2H), 6.20 (d, 1H), 4.50 (m, 1H), 3.20 (m, 2H), 2.70 (m, 1H), 2.00 (q, 2H), 1.80–1.40 (m, 5H), 1.20 (m, 1H), 0.90 (m, 12H).

The synthesis of compounds of general Formula 11–13 are summarized in Scheme II below:

Scheme II

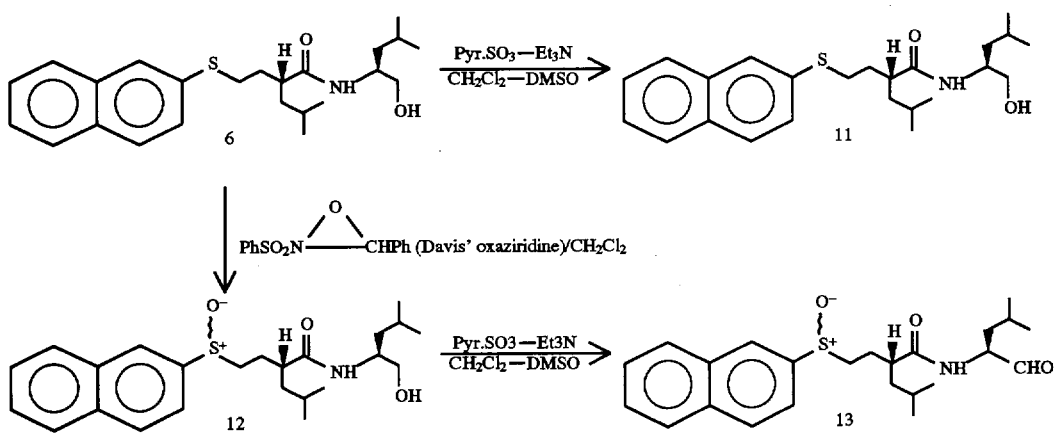

Example 7

Synthesis of Aldehyde 11

Aldehyde 11 was prepared from the intermediate compound 6 by oxidation with the sulfur trioxide-pyridine complex using a similar procedure to that described in Example 6 for the synthesis of aldehydes 9 and 10. Thus from 0.23 g of compound 6 there was obtained 0.12 g of compound 11.

Compound 11: White solid, mp 75°–76° C.; $R_f$ (70% ethyl acetate in hexanes): 0.85; $^1$H-NMR (300 MHz, CDCl$_3$) δ 9.60 (s, 1H), 7.80 (m, 4H), 7.45 (m, 3H), 5.90 (d, 1H), 4.60 (m, 1H), 3.20 (m, 1H), 2.90 (m, 1H), 2.60 (m, 1H), 2.00 (m, 1H), 1.80–1.40 (m, 5H), 1.40 (m, 1H), 1.20 (m, 1H), 0.90 (m, 12H).

Example 8

Synthesis of Intermediate 12

To a stirred solution of compound 6 (0.23 g, 0.573 mmol) in methylene chloride (4 mL) at room temperature was added a solution of Davis' oxaziridine (0.17 g, 0.58 mmol). The mixture was stirred for another 30 minutes and concentrated in vacuo to give a crude product. It was purified by silica gel column chromatography (eluant: 10% ethyl acetate in hexanes followed by 50% ethyl acetate in hexanes.) to give 0.21 g of compound 12 (diastereomeric mixture at the sulfoxide center). Davis' oxaziridine was prepared following the procedure of Davis et al. *J. Org. Chem.* 1988, 53, 2087.

Compound 12: White solid, mp 138°–140° C.; $R_f$ (ethyl acetate): 0.51; $^1$H-NMR (300 MHz, CDCl$_3$) δ 8.20 (s, 1H), 7.90 (m, 3H), 7.60 (m, 2H), 7.50 (m, 1H), 6.20 (q, 1H), 4.10 (m, 1H), 3.70 (m, 1H), 3.55 (m, 1H), 3.20 (q, 1H), 3.10–2.80 (m, 2H), 2.60 (m, 1H), 2.10–1.00 (a series of m, 8H), 0.90 (m, 12H).

Example 9

Synthesis of Aldehyde 13

Aldehyde 13 was prepared from the intermediate compound 12 by oxidation with the sulfur trioxide-pyridine complex using a similar procedure to that described in Example 6 for the synthesis of aldehydes 9 and 10. Thus from 0.160 g of compound 12 there was obtained 0.060 g of compound 13 (diastereomeric mixture at the sulfoxide center).

Compound 13: White solid, mp 134°–144° C. (softening to melt); $R_f$ (70% ethyl acetate in hexanes): 0.49; $^1$H-NMR (300 MHz, CDCl$_3$) δ 9.55 (d, 1H), 8.20 (d, 1H), 7.95 (m, 3H), 7.60 (m, 3H), 6.50 and 6.40 (2 sets of d, m), 4.50 (m, 1H), 3.10–2.80 (m, 2H), 2.70 (m, 1H), 2.10 (m, 1H), 1.90–1.40 (m, 6H), 1.25 and 1.10 (2 sets of m, 1H), 0.90 (m, 12H).

Example 10A

Inhibition of Cysteine Protease Activity

To evaluate inhibitory activity, stock solutions (40 times concentrated) of each compound to be tested were prepared in 100% anhydrous DMSO and 5 µL of each inhibitor preparation were aliquoted into each of three wells of a 96-well plate. Calpain I, prepared by a modification of the method of W. J. Lee et al. (*Biochem. Internatl.* 22: 163–171 (1990)), was diluted into assay buffer (i.e., 50 mM Tris, 50 mM NaCl, 1 mM EDTA, 1 mM EGTA, and 5 mM β-mercaptoethanol, pH 7.5 including 0.2 mM Succ-Leu-Tyr-MNA) and 175 µL aliquoted into the same wells containing the independent inhibitor stocks, as well as to positive control wells containing 5 µL DMSO, but no compound. To start the reaction, 20 µL of 50 mM CaCl$_2$ in assay buffer was added to all wells of the plate, excepting three, which were used as background signal baseline controls. Substrate hydrolysis was monitored every 5 minutes for a total of 30 minutes using a Fluoroskan II fluorescence plate reader. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. For screening, compounds were tested at 10 µm. Compounds having 50% inhibition at 10 µM were considered active. The IC50s of inhibitors (i.e., the concentration yielding 50% inhibition) were determined from the percent decrease in the rates of substrate hydrolysis in the presence of five to seven different concentrations of the test compound. The results were plotted as % inhibition versus log inhibitor concentration and the IC50 was calculated from linear regression of the data.

To demonstrate activity against two other cysteine proteases, cathepsin B (Calbiochem, cat#219364) and cathepsin L (Calbiochem, cat#219402), assays were performed substantially the same as outlined above except that the cathepsin B and cathepsin L were diluted into a different assay buffer consisting of 50 mM sodium acetate (pH 6.0)/1mM EDTA/1mM dithiothreitol and the substrate used was Cbz-Phe-Arg-AMC (Bachem cat# I-1160; 0.1 mM for cathepsin B; 0.006 mM for cathepsin L). Additionally, the order of reagents added to the plate was altered because both enzymes are constitutively active. Following inhibitor addition to the plates, appropriate 2× concentrated stock dilutions of the enzyme preparations were made in assay buffer and 10 ul added to each well.

The assay was initiated by addition of 100 ul of 2× concentrated stock dilution of substrate in assay buffer. Substrate hydrolysis was monitored using a Fluoroskan II (ex=390 nm; em=460 nm). Results are presented in Table II.

Example 10B

Inhibition of Serine Protease Activity

To demonstrate activity against the serine protease α-chymotrypsin (Sigma Chem. Co. Cat. #C-3142) the protocol of Example 10A was followed except that the enzyme was diluted into assay buffer consisting of 50 mM Hepes (pH 7.5)/0.5M NaCl and the final substrate concentration used was 0.03 mM SuccAla-Ala-Pro-Phe-AMC (Bachem, Inc. Cat. #I-1465). Additionally, because α-chymotrypsin is not a calcium sensitive enzyme and is constitutively active, following addition of inhibitor stocks to the 96 well plates, 100 μl of a 2-fold concentrated stock of enzyme in dilution buffer was first added and the reaction started by addition of 10 μl of a 2-fold concentrated stock of substrate in assay buffer. Substrate hydrolysis was monitored every 5 minutes up to 30 minutes using a Fluoroskan II (em=390 nm ex=460 nm). The result is expressed as inhibition of α-chymotrypsin at 10 μM.

Inhibition of thrombin (Sigma Chem. Co. Cat. #T-7009) was evaluated as described for chymotrypsin except that the assay was performed in 50 mM Tris, 10 mM CaCl$_2$, pH 7.5 and the substrate was 25 μM Bz-Phe-Val-Arg-AMC (Bachem cat#I-1080). Results are presented in Table II.

embodiments of the invention without departing from the spirit of the invention. It is intended that all such variations fall within the scope of the invention.

What is claimed is:

1. A compound of the structure:

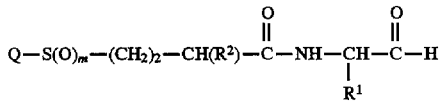

wherein:

Q is aryl having from 6 to 14 carbons, heteroaryl having from 6 to 14 ring atoms, aralkyl having from 7 to 15 carbons, heteroalkyl having from 2 to 7 carbons, or arylheteroalkyl wherein the aryl portion can be unfused or fused with the heteroalkyl ring;

m is 0, 1, or 2;

$R^1$ and $R^2$ are independently H, alkyl having from 1 to 14 carbons, cycloalkyl having 3 to 10 carbons, or a natural or unnatural side chain of an L-amino acid, said alkyl and cycloalkyl groups being optionally substituted with one or more J groups; and J is halogen, lower alkyl, aryl, heteroaryl, amino optionally substituted with one to three aryl or lower alkyl groups, guanidino, alkoxycarbonyl, alkoxy, hydroxy, or carboxy.

2. The compound of claim 1 wherein $R^1$ is selected from the group consisting of isobutyl, benzyl, and ethyl.

3. The compound of claim 2 wherein $R^2$ is isobutyl.

4. The compound of claim 3 wherein $R^2$ is isobutyl.

5. The compound of claim 1 wherein Q is aryl.

6. The compound of claim 2 wherein Q is aryl.

7. The compound of claim 6 wherein Q is 2-naphthyl.

8. The compound of claim 1 wherein m is 0.

9. The compound of claim 1 wherein m is 1.

10. The compound of claim 4 wherein m is 2.

11. The compound of claim 7 wherein m is 0.

12. The compound of claim 7 wherein m is 1.

13. The compound of claim 7 wherein m is 2.

14. The compound of claim 13 wherein $R^1$ and $R^2$ are each isobutyl.

15. A composition for inhibiting a serine protease or a cysteine protease comprising a compound of the structure:

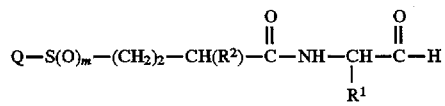

TABLE II

| Cpd. | Chemical Name | Calpain IC50 (nM) | Cat B IC50 (nM) | Cat L IC50 (nM) | Thrombin % I @ 10 μM | Chymotrypsin % I @ 10 μM |
|---|---|---|---|---|---|---|
| 9 | 2-Naphthylsulfonyl—CH$_2$CH$_2$CH(iBu)CO—Leu—H | 500 | 4500 | 32 | 2 | 12 |
| 10 | 2-Naphthylsulfonyl—CH$_2$CH$_2$CH(iBu)CO—Leu—H | 50 | 150 | 3 | 1 | 11 |
| 11 | 2-Naphthyl—SCH$_2$CH$_2$CH(iBu)CO—Leu—H | 75 | 60 | 8 | 5 | 11 |
| 13 | 2-Naphthyl—S(O)—CH$_2$CH$_2$CH(iBu)CO—Leu—H | 30 | 60 | 3 | 2 | 18 |

It is intended that each of the patents, publications, and other published documents mentioned or referred to in this specification be herein incorporated by reference in their entirety.

As those skilled in the art will appreciate, numerous changes and modifications may be made to the preferred wherein:

Q is aryl having from 6 to 14 carbons, heteroaryl having from 6 to 14 ring atoms, aralkyl having from 7 to 15 carbons, heteroalkyl having from 2 to 7 carbons, or arylheteroalkyl wherein the aryl portion can be unfused or fused with the heteroalkyl ring;

m is 0, 1, or 2;

$R^1$ and $R^2$ are independently H, alkyl having from 1 to 14 carbons, cycloalkyl having 3 to 10 carbons, or a natural or unnatural side chain of an L-amino acid, said alkyl and cycloalkyl groups being optionally substituted with one or more J groups; and J is halogen, lower alkyl, aryl, heteroaryl, amino optionally substituted with one to three aryl or lower alkyl groups, guanidino, alkoxycarbonyl, alkoxy, hydroxy, or carboxy.

16. A method for inhibiting serine proteases or cysteine proteases comprising contacting a protease selected from the group consisting of serine proteases and cysteine proteases with an inhibitory amount of a compound of the structure:

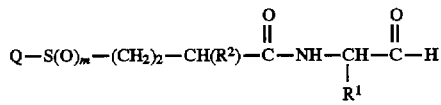

wherein:

Q is aryl having from 6 to 14 carbons, heteroaryl having from 6 to 14 ring atoms, aralkyl having from 7 to 15 carbons, heteroalkyl having from 2 to 7 carbons, or arylheteroalkyl wherein the aryl portion can be unfused or fused with the heteroalkyl ring;

m is of 1, or 2;

$R^1$ and $R^2$ are independently H, alkyl having from 1 to 14 carbons, cycloalkyl having 3 to 10 carbons, or a natural or unnatural side chain of an L-amino acid, said alkyl and cycloalkyl groups being optionally substituted with one or more J groups; and J is halogen, lower alkyl, aryl, heteroaryl, amino optionally substituted with one to three aryl or lower alkyl groups, guanidino, alkoxycarbonyl, alkoxy, hydroxy, or carboxy.

* * * * *

UNITED STATES PATENT AND TRADEMARK OFFICE
CERTIFICATE OF CORRECTION

PATENT NO. : 5,744,339  
DATED : Apr. 28, 1998  
INVENTOR(S) : Chatterjee

Page 1 of 4

It is certified that error appears in the above-indentified patent and that said Letters Patent is hereby corrected as shown below:

On the title page, under "OTHER DOCUMENTS", second column, at "Lee", please delete "Bindingsof" and insert --Bindings of--.

In column 1, line 56, please delete "*Trypoanosoma*" and insert --*Trypanosoma*--.

In column 1, line 63, please delete "ascade," and insert --cascade,--.

In column 2, line 59, please delete "arena,," and insert --arena,--.

In column 4, lines 35-40, please delete

"
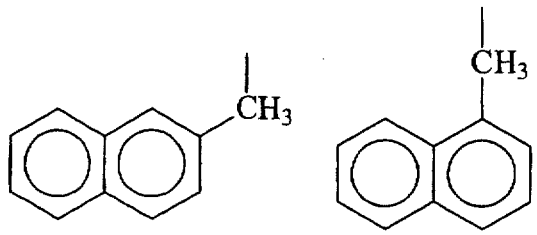
"

UNITED STATES PATENT AND TRADEMARK OFFICE
CERTIFICATE OF CORRECTION

PATENT NO. : 5,744,339
DATED : Apr. 28, 1998
INVENTOR(S) : Chatterjee

It is certified that error appears in the above-indentified patent and that said Letters Patent is hereby corrected as shown below:

and insert

--

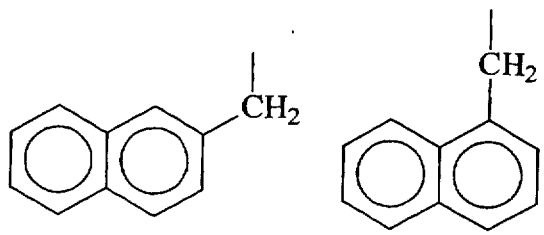

--.

In column 9, line 42, at the beginning of the line, please delete "(m, 1H),," and insert --(m, 1H),--.

In column 10, line 7, please delete "0.70 g" and insert --0.070 g-- therefor.

In column 10, line 39, please delete "(19 mL)" and insert --(10 mL)--.

UNITED STATES PATENT AND TRADEMARK OFFICE
CERTIFICATE OF CORRECTION

PATENT NO. : 5,744,339
DATED : Apr. 28, 1998
INVENTOR(S) : Chatterjee

It is certified that error appears in the above-indentified patent and that said Letters Patent is hereby corrected as shown below:

In column 12, lines 1-8, please delete

"
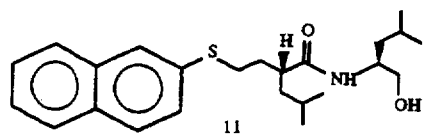

and insert

--
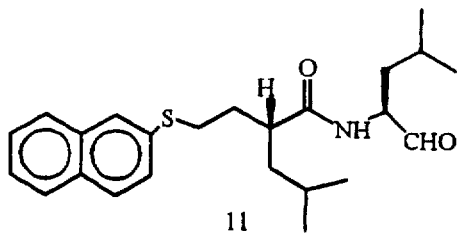

--.

UNITED STATES PATENT AND TRADEMARK OFFICE
CERTIFICATE OF CORRECTION

PATENT NO. : 5,744,339
DATED : Apr. 28, 1998
INVENTOR(S) : Chatterjee

It is certified that error appears in the above-indentified patent and that said Letters Patent is hereby corrected as shown below:

In column 13, line 18, please delete "10 ul" and insert --100 ul--.

In column 13, line 33, please delete "SuccAla-Ala-Pro-Phe-AMC" and insert --Succ-Ala-Ala-Pro-Phe-AMC--.

In column 13, line 39, please delete "10 µl" and insert --100 µl--.

In column 16, claim 16, line 13, please delete "is of" and insert --is 0,--.

Signed and Sealed this

Nineteenth Day of October, 1999

Attest:

Q. TODD DICKINSON

Attesting Officer

Acting Commissioner of Patents and Trademarks